July 29, 1969 W. FLEMER III Plant Pat. 2,912
CRAB APPLE TREE
Filed Oct. 5, 1967
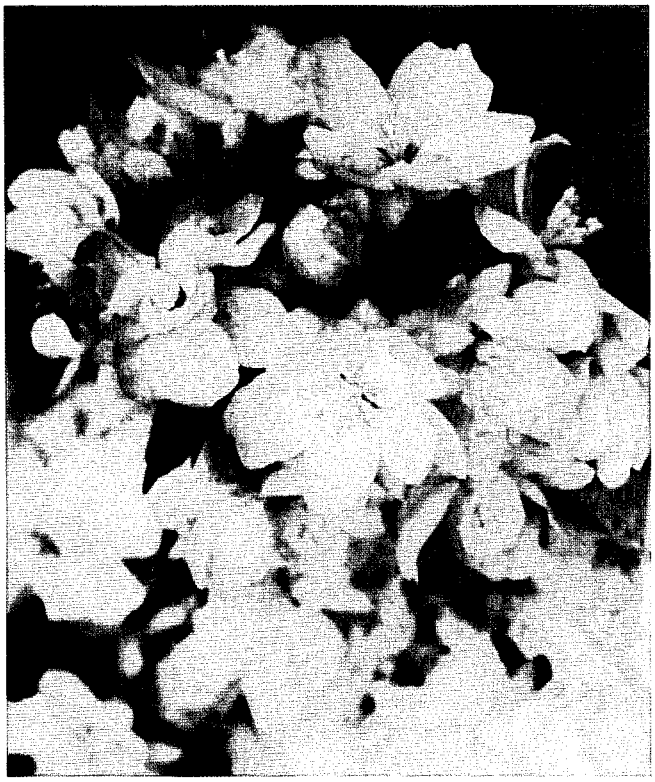
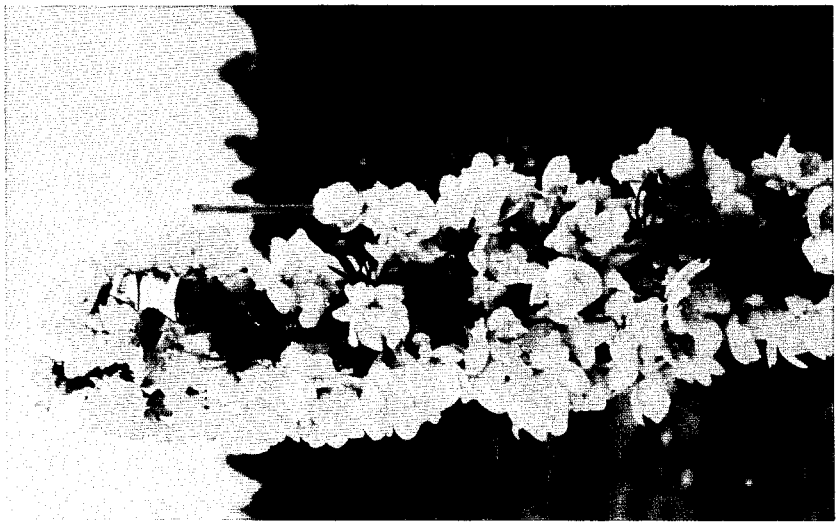
Inventor.
William Flemer, III
By: Robb & Robb
Attorneys.

United States Patent Office

Plant Pat. 2,912
Patented July 29, 1969

2,912

CRAB APPLE TREE

William Flemer III, Princeton, N.J., assignor to Treesearch, Kingston, N.J., a partnership

Filed Oct. 5, 1967, Ser. No. 673,237
Int. Cl. A01h *5/08*
U.S. Cl. Plt.—34 1 Claim

The present invention relates to a new and distinct variety of flowering crab apple tree which was originated by me by crossing the crab apple variety known as Malus "Katherine" (unpatented) with the crab apple variety known as Malus "Almey" (unpatented).

As the result of this breeding, I have produced a new and improved flowering crab apple variety which is distinguished from its parents, as well as from all other crab apple varieties of which I am aware, as evidenced by the following unique combination of characteristics which are outstanding therein:

(1) An exceptional vigorous habit of growth as compared with other pink varieties;

(2) A non-defoliating habit under unfavorable weather conditions attributable to relatively high summer temperatures and humidity which prevail in New Jersey.

(3) Large, double flowers which are borne in clusters so densely as to hide the tree branches;

(4) A clear pale pink flower color which is retained until the petals drop;

(5) A high resistance to fire blight; and (6) Sparse fruit production and freedom of fruit disfiguration by apple scab disease.

Asexual reproduction of my new variety, as performed by bud-grafting in Plainsboro Township, N.J., shows that the foregoing characteristics and distinctions come true to form and are established and transmitted through succeeding propagations.

The accompanying drawing shows a typical specimen of the top portion of a young tree of my new variety, and typical flowers as depicted on a somewhat enlarged scale, all as depicted in color as nearly true as it is reasonably possible to make the same in a color illustration of this character.

The following is a detailed description of my new variety, with color terminology in accordance with the Munsell Color Chart, except where general color terms of ordinary dictionary significance are obvious:

Parentage: Seedling.
- *Seed parent.*—M. "Katherine."
- *Pollen parent.*—M. "Almey."

Propagation: Holds its distinguishing characteristics through succeeding propagations by bud-grafting.

Locality where grown and observed: Plainsboro, Township, N.J.

Tree: Medium size; upright; tall; dense; hardy; exceptionally vigorous in growth habit which is twice the usual growth rate of such varieties as those of the botanical species known as *Malus scheideckeri* or of the parent variety "Katherine," for example.
- *Trunk.*—Stocky; smooth.
- *Branches.*—Stocky; smooth. Lenticals—sparse in number. Color—Moderate Olive Green, Hue 2.5GY 4/3.

Foliage:
- *Leaves.*—Abundant; thick. Size: Length—about 9 cm. (not including petiole), width—about 4.5 cm. Shape—ovate; pointed. Color—Dark green, Hue 5G 3/4. Margin—serrate; some basal leaves bear one lobe on vigorous shoots. Petiole—medium length (about 2.1 cm. long). Glands—none. Stipules;—about 1.5 cm. long.

Flower buds: Hardy; clustered.
- *Size.*—Length—about 1.5 cm. Width—about 2 cm.
- *Clusters.*—6 or 7 per cluster.
- *Shape.*—Globular.
- *Color.*—Strong Purplish Red, Hue 10RP 4/12.

Flowers:
- *Blooming season.*—First bloom—about May 3 in central New Jersey. Full bloom—about May 8 in central New Jersey.
- *Quantity.*—Very abundant.
- *Size.*—Very large (from 5 cm. to 6 cm. in diameter).
- *Color (when fully open).*—Generally pale pink ranging from near Light Purplish Pink, Hue 2.5RP 8/5 to near Strong Pink, Hue 10RP 7/8, but sometimes becoming nearly white as the flowers age.
- *Petalage.*—Number of petals—15 or 16. Shape of petals—round; ovate. Size of petals: Length—from 2.5 cm. to 3 cm., width—about 2.2 cm.

Fruit:
- *Borne.*—September–October.
- *Quantity.*—Sparse.
- *Shape.*—Slightly lobed; slightly pyriform.
- *Size.*—Length—about 1.5 cm. width—about 1.4 cm.
- *Color.*—Vivid Greenish Yellow, Hue 7.5Y 8/12.

I claim:

1. A new and distinct variety of flowering crab apple tree, substantially as herein shown and described, characterized particularly as to novelty by the unique combination of an exceptional vigorous habit of growth as compared with other pink flowered varieties, a non-defoliating habit under unfavorable weather conditions prevalent in New Jersey, large, double flowers which are borne in clusters so densely as to hide the tree branches, a clear pale pink flower color which is usually retained until the petals drop, a high resistance to fire blight and sparse fruit production and freedom of fruit disfiguration by apple scab disease.

No references cited.

ROBERT E. BAGWILL, Primary Examiner